(12) United States Patent
Huellen et al.

(10) Patent No.: US 11,284,817 B2
(45) Date of Patent: Mar. 29, 2022

(54) METHOD FOR DETERMINATION OF AN ANALYTE CONCENTRATION IN A BODY FLUID AND ANALYTE CONCENTRATION MEASUREMENT DEVICE

(71) Applicant: Roche Diabetes Care, Inc., Indianapolis, IN (US)

(72) Inventors: Volker Huellen, Mannheim (DE); Max Berg, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 506 days.

(21) Appl. No.: 16/381,869

(22) Filed: Apr. 11, 2019

(65) Prior Publication Data
US 2019/0239781 A1  Aug. 8, 2019

Related U.S. Application Data

(63) Continuation of application No. PCT/EP2017/077137, filed on Oct. 24, 2017.

(30) Foreign Application Priority Data

Oct. 25, 2016 (EP) .................................... 16195524

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0059* (2013.01); *A61B 5/1455* (2013.01);
(Continued)

(58) Field of Classification Search
CPC .......... A61B 2562/0257; A61B 5/0059; A61B 5/14532; A61B 5/1455; A61B 5/14552;
(Continued)

(56) References Cited

U.S. PATENT DOCUMENTS 6,192,261 B1   2/2001 Gratton et al.
2002/0146835 A1* 10/2002 Modzelewski .... G01N 21/8483
436/95
(Continued)

FOREIGN PATENT DOCUMENTS

CN   101917899 A   12/2010
CN   102469965 A   5/2012
(Continued)

OTHER PUBLICATIONS

International Search Report and Written Opinion of the International Searching Authority, PCT/EP2017/077137, dated Jan. 17, 2018, 7 pages.
(Continued)

*Primary Examiner* — Jennifer Wecker
*Assistant Examiner* — Kathryn Elizabeth Limbaugh
(74) *Attorney, Agent, or Firm* — Bose McKinney & Evans LLP

(57) ABSTRACT

Disclosed is a method of using a handheld meter configured for determining an analyte concentration in a body fluid. In the inventive method, a handheld meter with a disposable test element is provided and the test element is positioned at an application site of the meter. A body fluid from a user's body part is applied to a reaction area of the test element and a series of measurement values from the reaction area of the test element is detected. A proximity sensor senses the presence of the body part in a monitored space in proximity to the reaction area of the test element. The measured values are processed as a function of an output signal of the proximity sensor. Consequently, bias in the determination of the analyte concentration caused by the presence of the body portion is reduced or eliminated. An associated handheld meter is also disclosed.

18 Claims, 3 Drawing Sheets

(51) Int. Cl.
*A61B 5/1455* (2006.01)
*G01N 21/78* (2006.01)
*A61B 5/151* (2006.01)
*A61B 5/157* (2006.01)

(52) U.S. Cl.
CPC .......... *A61B 5/14552* (2013.01); *A61B 5/157* (2013.01); *A61B 5/15101* (2013.01); *A61B 2562/0257* (2013.01); *G01N 21/78* (2013.01)

(58) Field of Classification Search
CPC ..... A61B 5/15101; A61B 5/157; A61B 5/145; A61B 10/0045; G01N 21/78; G01N 33/48785
See application file for complete search history.

(56) References Cited

U.S. PATENT DOCUMENTS

| | | |
|---|---|---|
| 2003/0212344 A1 | 11/2003 | Yuzhakov et al. |
| 2005/0157304 A1 | 7/2005 | Xiao et al. |
| 2006/0173379 A1 | 8/2006 | Rasch-Menges et al. |
| 2007/0181784 A1 | 8/2007 | Twiney et al. |
| 2010/0094112 A1 | 4/2010 | Heller et al. |
| 2010/0144048 A1 | 6/2010 | Petrich |
| 2011/0105867 A1 | 5/2011 | Schultz et al. |
| 2011/0223078 A1 | 9/2011 | Ohashi |
| 2012/0238840 A1 | 9/2012 | Hashimoto |
| 2014/0041443 A1 | 2/2014 | Eikmeier et al. |
| 2014/0360873 A1 | 12/2014 | Richter et al. |
| 2015/0176053 A1 | 6/2015 | Elder et al. |
| 2015/0238131 A1 | 8/2015 | Richter et al. |
| 2015/0268228 A1 | 9/2015 | Schulat et al. |
| 2015/0330937 A1* | 11/2015 | Guthrie ............ G01N 33/48785 205/792 |
| 2016/0033440 A1 | 2/2016 | Cho et al. |
| 2017/0143210 A1 | 5/2017 | Ikebe |

FOREIGN PATENT DOCUMENTS

| | | |
|---|---|---|
| CN | 102680449 A | 9/2012 |
| CN | 104144645 A | 11/2014 |
| CN | 104159509 A | 11/2014 |
| CN | 104838258 A | 8/2015 |
| CN | 105188561 A | 12/2015 |
| CN | 105849544 A | 8/2016 |
| EP | 0 623 307 A1 | 11/1994 |
| JP | H 09-167952 A | 6/1997 |
| JP | 2007-206078 A | 8/2007 |
| JP | 2012-075750 A | 4/2012 |
| JP | 2014-075690 A | 4/2014 |
| KR | 10-2014-0012709 A | 2/2014 |
| TW | 201604541 A | 2/2016 |
| WO | WO 02/070734 A1 | 9/2002 |
| WO | WO 2013/055962 A1 | 4/2013 |
| WO | WO 2014/126482 A2 | 8/2014 |
| WO | WO 2015/151508 A1 | 10/2015 |
| WO | WO 2015/173417 A1 | 11/2015 |

OTHER PUBLICATIONS

International Preliminary Report on Patentability, PCT/EP2017/077137, dated Apr. 30, 2019, 5 pages.

* cited by examiner

METHOD FOR DETERMINATION OF AN ANALYTE CONCENTRATION IN A BODY FLUID AND ANALYTE CONCENTRATION MEASUREMENT DEVICE

RELATED APPLICATIONS

This application is a continuation of PCT/EP2017/077137, filed on Oct. 24, 2017, which claims priority to EP 16 195 524.0, filed Oct. 25, 2016, the entire disclosures of which are hereby incorporated herein by reference.

BACKGROUND

This disclosure concerns a method for determination of an analyte concentration in a body fluid. The disclosure further concerns an analyte concentration measurement device.

In the field of blood glucose testing, it is known to provide a handheld glucose meter with several test elements for multiple successive tests. Specifically, test elements can be provided as chemistry fields on a test tape, which is loadable into the meter in the form of a replaceable tape cassette. Thus, the user has no need to take care of the disposal of each single test element. However, the instrument is generally used by patients outside a laboratory environment, and therefore the measurement may be susceptible to non-intended user handling. In extreme cases of user handling scenarios, significant measurement deviations may occur.

From WO 2015/173417 A1 it is known to provide a hand-held test meter for use with test strips in the determination of glucose in a bodily fluid sample. For saving battery power, a proximity sensor module is configured to detect the presence of a user's body in order to switch the meter from standby to active mode.

U.S. Publication No. 2015/0238131 A1 proposes to employ a proximity sensor to determine whether a body part of a user protrudes by a required amount within a housing aperture such that a lancing and blood collecting operation will be successful with a high degree of confidence. This document is not concerned with instrument handling during the ultimate measurement procedure, as the sample handling and processing is carried out in a fully automated way inside the housing.

SUMMARY

This disclosure improves the known measuring methods and systems to enhance the accuracy and precision of the measurement results by controlled user handling during the data acquisition phase or detection phase.

This disclosure is based on the idea of preventing measurements from being distorted by the presence of a body part. Thus, a method for determination of an analyte and specifically glucose in a body fluid is proposed according to this disclosure which comprises the steps of:
  providing a disposable test element at an application site in a handheld meter,
  providing a body fluid on a user's body portion (body part) and applying the body fluid on a reaction area of the test element,
  detecting, by means of a preferably photometric detection unit of the meter, a series of measuring values from the reaction area of the test element, and determining the analyte concentration at least in part from the series of measuring values,
  employing a proximity sensor disposed within the meter to sense the presence of the body portion (body part) in a monitored space in proximity to the reaction area of the test element, and
  controlling the processing of the measuring values depending on an output signal of the proximity sensor to avoid a bias in the determination of the analyte concentration caused by the presence of the body portion.

It should be noted that these steps need not necessarily be carried out in a strict chronological order. For example, the signals of the detection unit and the proximity sensor may be processed in parallel. By all means, these measures provide for a regular data processing during detected absence of the user's body portion, where apparently the user does not adversely impact the measurement. On the other hand, in case of a detected proximity of the user's body, possible countermeasures allow safeguarding against non-intended use and ultimately ensure a correct test result or a discarded test result. It is also possible to provide appropriate feedback to the user. This disclosure is specifically useful in cases where the user himself has to apply a sample in a forth and back movement of a body part, in particular a finger, and where unintentional prolonged presence intervenes an optical measuring path of the device.

Advantageously, a warning is provided to the user upon sensing the presence of the body portion (body part) in the monitored space. Such a warning may contribute to optimization of user handling.

As a still stronger counteractive measure, it is also advantageous when the detection of measuring values is aborted and/or an error message is provided by the meter when prolonged presence of the body portion is observed in the monitored space.

Another improvement in this direction provides for measuring a time interval of the presence of the body portion in the monitored space, and for aborting the detection of measuring values and/or providing an error message to the user when the time interval exceeds a predetermined length.

In order to account for specific sample application procedure, a wetting of the test element with body fluid is detected, and measuring of the time interval is started at the point in time when detecting the wetting.

Preferably, the length of the time interval is in the range of 0.5 to 2 s.

In order to account for intended use, the detection of measuring values is completed only if the body portion is not present in the monitored space.

For a possible immediate intervention in the measuring process, it is also advantageous when the output signal of the proximity sensor is made available as an input for a processor unit of the meter during processing of the measuring values.

It is further advantageous when the output signal of the proximity sensor is processed differently during at least two measuring phases. In this way, multiple benefits may be achieved from the implementation of the proximity sensor.

For a dedicated discrimination of a problematic proximity it is advantageous to configure the proximity sensor such that the monitored space includes a cuboid in the size of at least 1×1×5 mm, preferably at least 3×3×10 mm, where the long side of the cuboid is perpendicular to a surface of the test element.

Preferably, the output signal of the proximity sensor is provided as a digital value indicating solely the presence or absence of the body portion in the monitored space.

According to a preferred implementation, the detection of measuring values comprises an initial measuring phase for measuring a blank value on the test element prior to body fluid application, an intermediate measuring phase for tracking a development of the measuring values, and a final measuring phase for determining an end value which is characteristic for a quantity of the analyte.

A further improvement in this connection comprises transporting the test element on a transport tape over a deflection tip as a sample application site, and arranging the proximity sensor adjacent or in close proximity to the deflection tip.

A still further improvement provides that the body fluid is applied on a freely accessible application side of the test element, and the measuring values are detected by scanning a back side of the test element opposite to the application side.

Another aspect of this disclosure concerns an analyte concentration measurement device, in particular for blood glucose determination, comprising a handheld meter adapted to provide a disposable test element having a reaction area at an application site for applying body fluid from a user's body portion (body part), a preferably photometric detection unit operable for detecting measuring values on or from the reaction area of the test element, and a proximity sensor disposed within the meter to sense the presence of the body portion in a monitored space in proximity to the reaction area of the test element, wherein a processor unit of the meter is configured for:
 i. processing the measuring values for determining the analyte concentration, and
 ii. processing the measuring values depending on an output signal of the proximity sensor to avoid a bias in the determination of the analyte concentration caused by the presence of the body portion.

Such a device allows for carrying out the inventive method to achieve the same advantages as outlined above.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

Figure 1:
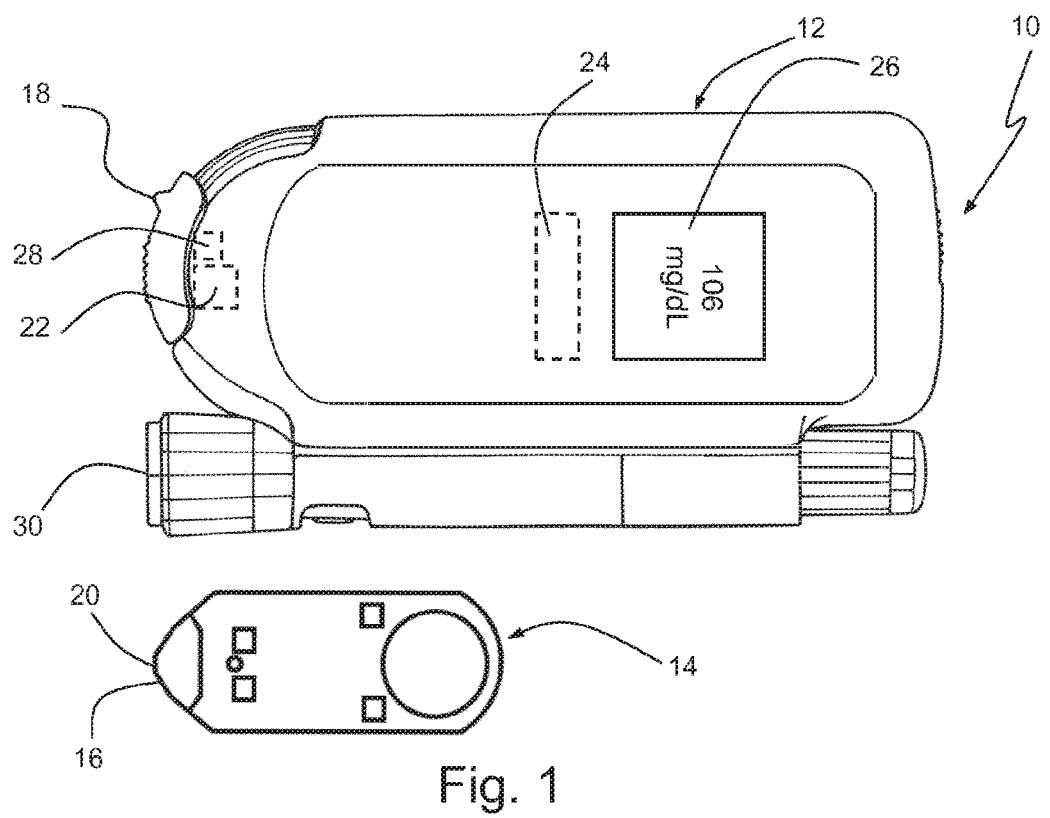
FIG. 1 shows a testing system including a handheld blood glucose meter configured for using a test tape cassette.

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

In the drawings, an exemplary embodiment of a medical analyte testing system for testing an analyte in a body fluid, specifically glucose in a blood sample is shown.

As depicted in FIG. 1, the system 10 at least comprises a portable blood glucose meter 12 adapted to receive a disposable test tape cassette 14 (shown separately) which can be inserted into a compartment of the meter 12. A tip 16 of the inserted tape cassette 14 is accessible to the user upon opening a tip cover 18. The tape cassette 14 serves as a test magazine, as a plurality of test elements 20 is provided on a spoolable transport tape for successive use on the tip 16.

The handheld meter 12 is provided with a photometric measuring unit (measuring instrument) 22 and a processor unit 24 (electronic micro-processor) for determining the concentration of the analyte from the measured values. Such electronic processors for determining the concentration of an analyte from measured values of, e.g., frequency or wavelength of light reflected from the test area, are known to those of skill in the art. The measuring result and other information can be displayed to the user on a display 24. The meter 12 is further provided with a proximity sensor 28 to detect the presence of a body part during critical measuring phases, thus allowing to control user handling. Optionally, a lancing aid 30 is attached to the meter 12 for simplifying lancing of a body part in order to sample blood.

Figure 2:
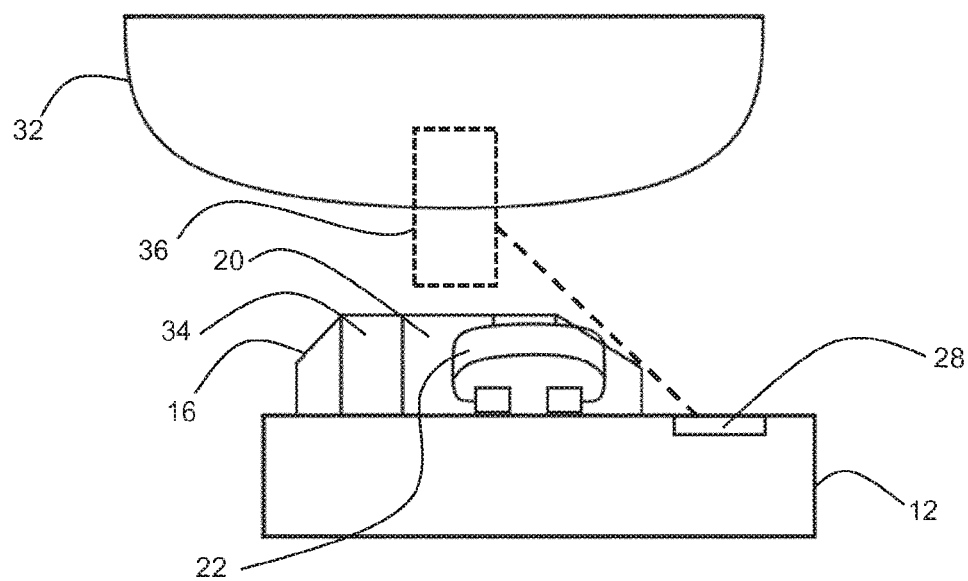
FIG. 2 is an extended section of the meter and a user's finger in proximity to a test element.

FIG. 2 depicts a handling situation in a partial cross section of the system 10 transverse to the tip 16 of the inserted tape cassette 14. For carrying out an analyte test, the user applies a drop of blood from his finger 32 to a top side of the active test element 22 provided on the tip 16. The test element 22 is formed by a layered chemistry field on the transport tape 34 which is responsive to the analyte by a color change. Then, the measuring unit 22 provided as a reflectometer allows a measurement of the analyte concentration by optical scanning the rear side of test element 22 through the transparent transport tape 34.

However, the measurement may be biased by the presence of the finger 32 which appears to the reflectometer as a dark background behind the incompletely opaque chemistry field. This influence increases with decreasing distance of the finger 32 to the critical test field area. In another adverse user handling scenario, continued finger pressure on the test element 22 after sample application may lead to an unwanted modification of the layered test structure, specifically if a covering net provided for sample spreading is impressed into the chemistry field such that the optical measurement is impaired thereby.

Thus, the proximity sensor 28 is configured to sense the presence of the body portion (body part, typically a finger) in a monitored space 36 in proximity to the test element 22. The proximity sensor 28 is purposely placed laterally to the tape 34 adjacent to the tip 16.

The favored solid angle that will be surveilled by the proximity sensor 28 should be as much as possible restricted. It should be ensured that the sensor does not detect objects outside a specified detection area, especially any support surface like, e.g., a table. Ideally, the monitored space 36 should include a cuboid in the size of approximately 3×3×10 mm, where the long side of the cuboid is perpendicular to the top side of the test element 20. Furthermore, the optical analyte measuring unit 22 should not be disturbed by the proximity sensor 28.

As a further design consideration, the proximity sensor 28 should deliver a digital signal indicating solely the following cases:
 (0) false—no object detected;
 (1) true—object within defined space detected.

This signal should be available as an input for a measurement routine of the processor unit 24 while it is running.

The proximity sensor 28 may be formed as a kind of photometric sensor that can detect any kind of object. The working principle may be similar to that of the analyte measuring unit: Somehow modulated light is sent out by a light source (LED). Any reflected light is collected by a photo detector. Depending on the amount of reflected light, an analog signal is created. Via a set threshold, the digital discrimination between absence and presence of an object is made.

For a proximity detection, there are also other sensor types conceivable, namely inductive, capacitive and ultrasonic sensors to detect the presence or absence of objects.

Figure 3:
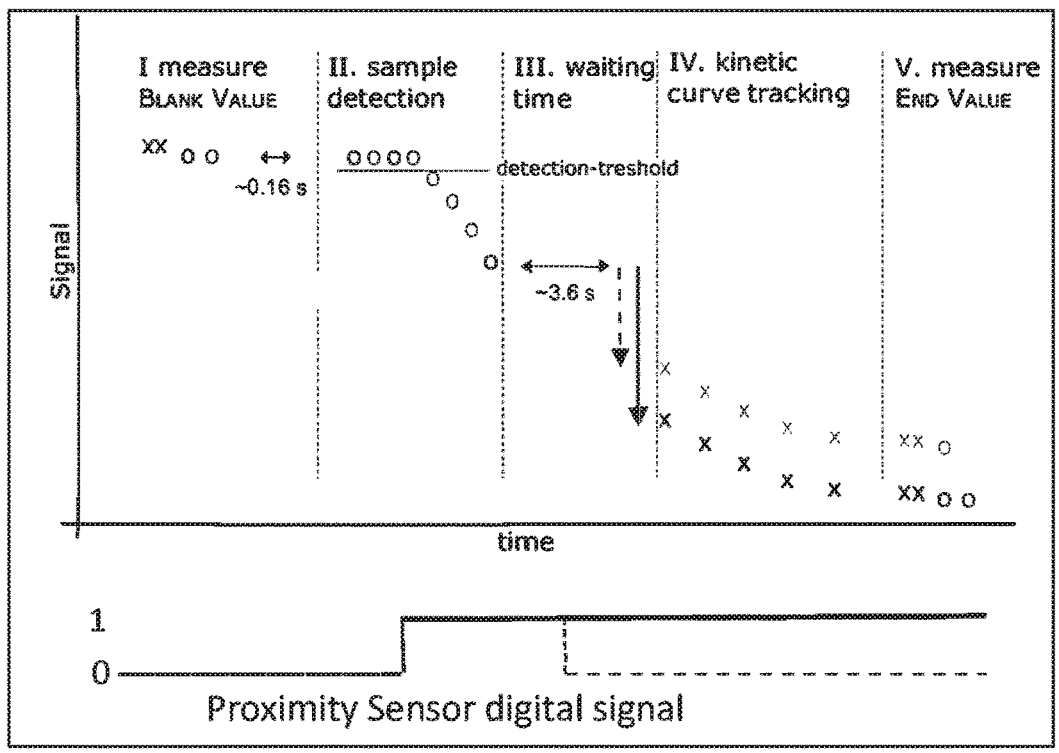
FIG. 3 is a time diagram of a measuring process including a proximity sensor signal.

As illustrated in FIG. 3, the measuring process may be divided in various measuring phases. The time diagram shows measuring values on a test element provided by using a main light source (symbol x) and at least one auxiliary light source (symbol o) of the measuring unit 22. In an initial measuring phase (phase I), a blank value is detected as a double-measurement on the yet unused test element 20 prior to sample application. Thereafter, the auxiliary light source is powered to enable wetting detection preferably at a different wavelength. In the following phase II, consecutive measuring values are registered with a given sampling rate of, e.g., 5 Hz to enable recognition of the wetting of the test element 22 due to sample application by the user. Such wetting leads to a signal decrease below a predetermined detection threshold. However, in the first seconds there is no reliable behavior of the reactive chemical layers of the test element 22 due to swelling and diffusion processes. Therefore, a predetermined waiting time should be observed in phase III.

Then, the chemical reaction due to the presence of the analyte can be tracked in phase IV, where the reaction product leads to an increasing darkening and hence to less reflected light. The kinetic curve exhibits an asymptotic behavior, such that a given stop criterion is reached after a plurality of measurement readings. Finally, in phase V, an end value is recorded, eventually followed by a control measurement for sufficiency of sample application. As a measurement result, the analyte concentration value is determined from the ratio of the end value to the blank value. All other measurements are only accessory to find this result.

FIG. 3 also shows a comparative measurement with intended use, i.e., absence of a body part 32 after the waiting time (upper curve associated with the dotted arrow shown in phase III), and with non-intended use, i.e. presence of the body part 32 (lower kinetic curve and continuous arrow in phase III). Associated therewith, the digital output signal of the proximity sensor 28 is shown below in dotted and continuous lines. It becomes readily apparent that the presence of the body part after sample application leads to a reduced background remission, which interferes with the measuring result quite remarkably.

The information obtained by the proximity sensor 28 in the meter 12 is processed differently during various measurement phases. If possible, appropriate feedback (visual, acoustic and/or haptic) is provided to the user, as explained in more detail below.

Figure 4:
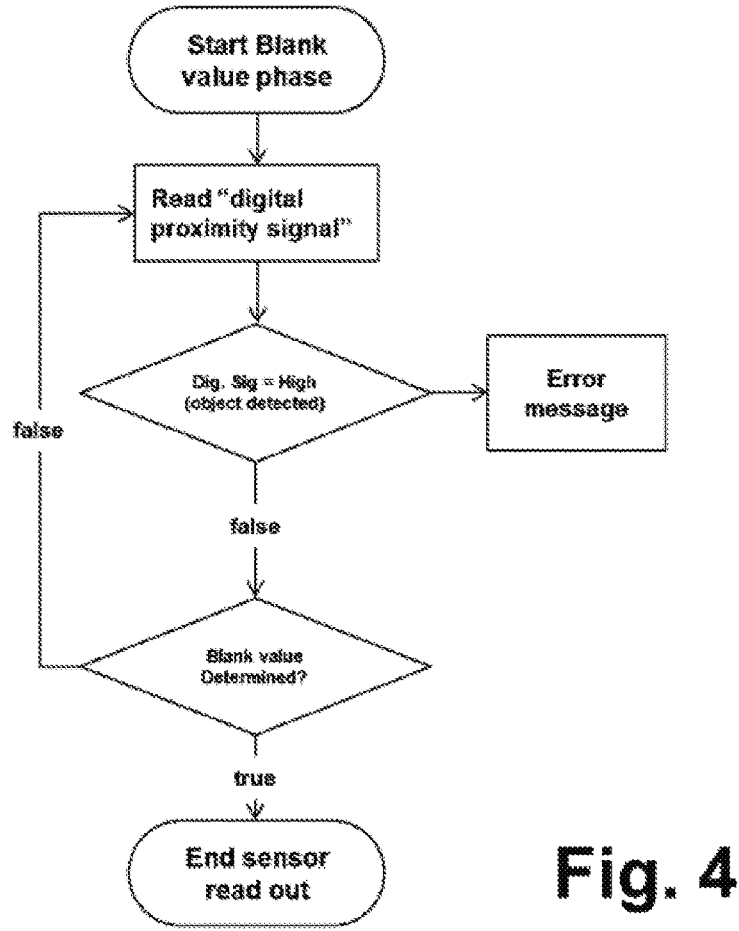
FIG. 4 is a flow-chart of a signal processing routine during a blank value measurement phase.

FIG. 4 shows a flow-chart of a signal processing routine of the processor 24 in phase I when measuring the blank value. In case no object (finger) is detected by the proximity sensor, the blank value can be determined without bias of the measuring unit 22. In the other case, where the object is in proximity to the test element 20, the blank value cannot be determined reliably and an error message is displayed as a feedback to the user.

Figure 5:
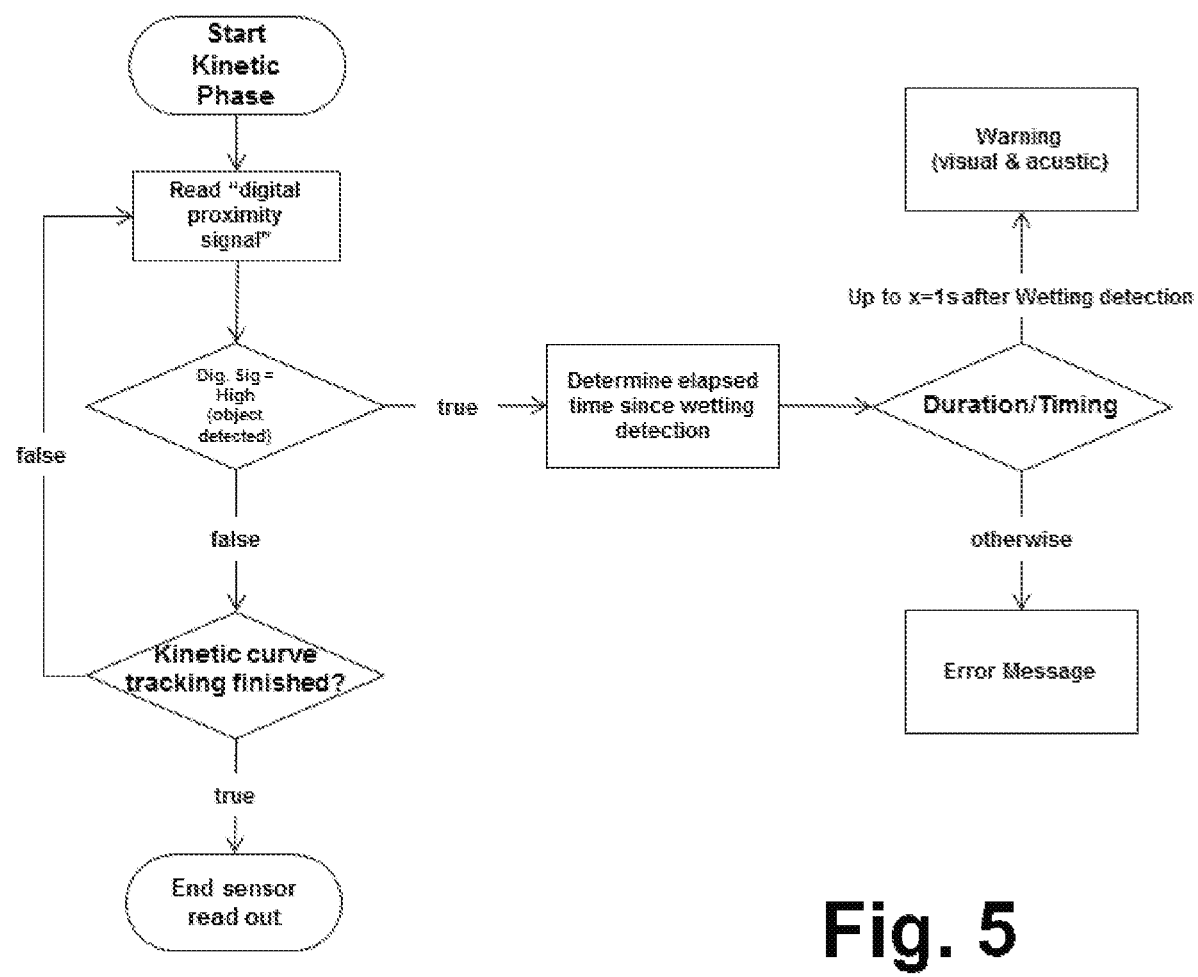
FIG. 5 is a flow-chart of a signal reading routine during a kinetic measurement phase.

FIG. 5 shows another operational principle of the signal processing routine (measuring engine) running in the processing unit 24 in phase III. Here, the kinetic curve tracking is accomplished when the object (body portion or body part) is not present in the monitored space. In this phase, the presence of the body portion may be tolerated for a given elapsed time since the wetting detection. Within this period, the user can be warned to remove his finger, such that the active test element 20 need not be discarded. Thereafter, an error message is displayed and the measurement is aborted.

As apparent from the above description, both the output signal of the proximity sensor 28 and the measuring values of the measuring unit 22 have to be supplied to the processing unit 24 for sequential or parallel processing. Furthermore, the processing unit 24 must be configured to evaluate the duration of the proximity signal.

It is also conceivable to employ the proximity sensor 28 for other surveillance tasks in the user handling of the meter 12. For example, in addition to the signal drop in phase II, a second confirmation of the blood application may be obtained by an evaluation of the proximity signal. This may be obtained comparing the digital proximity signal with empirical data for duration of object detection during wetting stored in a memory of the meter 12. Another option to employ the proximity sensor 28 would be to stop the tape transport while object recognition is positive to ensure a correct positioning of the test elements in the respective active position on the tip 16.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method of using a handheld meter configured for determining an analyte concentration in a body fluid, the method comprising:
   providing a handheld meter with a disposable test element positioned at an application site of the meter;
   applying a body fluid from a user's body part to a reaction area of the test element;
   detecting a series of measurement values from the reaction area of the test element;
   using a proximity sensor to sense the presence of the body part in a monitored space in proximity to the reaction area of the test element; and
   processing the measurement values as a function of an output signal of the proximity sensor, whereby bias or error in the determination of the analyte concentration caused by the presence of the body part is reduced or eliminated.

2. The method of claim 1, wherein a warning is provided to the user upon sensing the presence of the body part in the monitored space.

3. The method of claim 1, wherein the detection of measurement values is aborted and/or an error message is provided by the meter when the presence of the body part in the monitored space is detected.

4. The method of claim 1, further comprising:
   measuring a time interval of presence of the body part in the monitored space; and aborting the detection of measurement values and/or providing an error message to the user after a predetermined length of the time interval.

5. The method of claim 4, wherein a wetting of the test element with body fluid is detected and the time interval begins at the time of the detected wetting.

6. The method of claim 4, wherein the length of the time interval is in the range of 0.5 to 2 s.

7. The method of claim 1, wherein the detection of measurement values is completed only when the body part is not present in the monitored space.

8. The method of claim 1, wherein the output signal of the proximity sensor is input to a processor of the meter during the processing of the measurement values.

9. The method of claim 1, wherein the output signal of the proximity sensor is processed differently during at least two different periods of time during the detection of the measurement values.

10. The method of claim 1, wherein the monitored space includes a cuboid in the size of at least 1×1×5 mm, wherein the long side of the cuboid is perpendicular to a surface of the test element.

11. The method of claim 10, wherein the cuboid is in the size of at least 3×3×10 mm.

12. The method of claim 1, wherein the output signal of the proximity sensor is a digital value indicating the presence or absence of the body part in the monitored space.

13. The method of claim 1, wherein the detection of measurement values comprises an initial measuring phase for measuring a blank value on the test element prior to the applying of the body fluid, an intermediate measuring phase for tracking a development of the measurement values, and a final measuring phase for determining an end value which is characteristic for a quantity of the analyte.

14. The method of claim 1, further comprising transporting the test element on a transport tape over a deflection tip arranged at a sample application site and arranging the proximity sensor adjacent or in close proximity to the deflection tip.

15. The method of claim 1, wherein the body fluid is applied on a freely accessible application side of the test element and the measurement values are detected by scanning a back side of the test element opposite to the application side.

16. The method of claim 1, wherein the analyte is glucose.

17. The method of claim 1, wherein the detecting of measurement values comprises photometric detection with a photometric detection unit of the handheld meter.

18. An analyte concentration measurement device, comprising:
  a handheld meter configured for use with a disposable test element having a reaction area; and
  a proximity sensor configured to sense the presence of a body part in a monitored space in proximity to the reaction area of the test element; and
  a processor configured for:
    i) receiving measurement values detected at the reaction area; and
    ii) processing the measurement values as a function of an output signal of the proximity sensor.

* * * * *

UNITED STATES PATENT AND TRADEMARK OFFICE
CERTIFICATE OF CORRECTION

Page 1 of 1

PATENT NO. : 11,284,817 B2
APPLICATION NO. : 16/381869
DATED : March 29, 2022
INVENTOR(S) : Huellen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 509 days.

Signed and Sealed this
Eighteenth Day of February, 2025

Coke Morgan Stewart
*Acting Director of the United States Patent and Trademark Office*